United States Patent [19]

Pelletier et al.

[11] Patent Number: 5,569,586
[45] Date of Patent: Oct. 29, 1996

[54] NUCLEIC ACID PROBES FOR THE DETECTION OF BACTERIA OF THE GENUS LEGIONELLA AND METHODS FOR THE DETECTION OF THE ETIOLOGICAL AGENTS OF LEGIONNAIRES' DISEASE

[75] Inventors: Dale A. Pelletier, Southborough; William G. Weisburg, Milford, both of Mass.

[73] Assignee: Amoco Corporation, Chicago, Ill.

[21] Appl. No.: 309,560

[22] Filed: Sep. 20, 1994

Related U.S. Application Data

[63] Continuation of Ser. No. 66,373, May 24, 1993, abandoned.
[51] Int. Cl.$^6$ .............................. C12Q 1/68; C07H 21/04
[52] U.S. Cl. .......................... 435/6; 536/24.3; 536/24.32; 536/24.33
[58] Field of Search ............................. 435/6; 536/24.32, 536/23.1, 23.7, 24.3, 24.33; 935/78

[56] References Cited

U.S. PATENT DOCUMENTS 4,851,330  7/1989  Kohne .......................................... 435/6

FOREIGN PATENT DOCUMENTS

WO88/03957  6/1988  WIPO.

OTHER PUBLICATIONS

Fox et al., *Syst. Appl. Microbiol.* 11, 135–139 (1989).
Fox et al., *Syst. Appl. Microbiol* 14, 52–56 (1991).
*FEMS Microbiol. Lett.*, Böttger, vol. 65, 171–176 (1989).
*Am. J. Clin. Path.*, Fain et al., vol. 95(5), 719–724 (1991).

*Primary Examiner*—Kenneth R. Horlick
*Attorney, Agent, or Firm*—Norval B. Galloway

[57] ABSTRACT

Nucleic acid sequences which hybridize preferentially to the 16S or 23S rRNA or rDNA of Legionella sp., *L. pneumophila*, *L. micdadei*, a *L. pneumophila*, or a Legionella subset are taught. These organisms are the etiological agents of Legionnaires' disease, Pontiac fever, Pittsburgh pneumonia and other infections. The nucleic acids are useful in the detection of these pathogenic microorganisms. Probes based on these sequences and kits containing the probes are also disclosed.

19 Claims, 1 Drawing Sheet

NUCLEIC ACID PROBES FOR THE DETECTION OF BACTERIA OF THE GENUS LEGIONELLA AND METHODS FOR THE DETECTION OF THE ETIOLOGICAL AGENTS OF LEGIONNAIRES' DISEASE

This is a continuation of application Ser. No. 08/066,373, filed May 24, 1993, now abandoned.

This invention relates to nucleic acids, probes, kits, and methods for the detection of pathogenic organisms, including Legionella sp., believed to be involved with Legionnaire's disease, Pontiac fever, Pittsburgh pneumonia, and several other diseases.

BACKGROUND OF THE INVENTION

Legionella were first discovered in 1976 following an outbreak of 182 cases of pneumonic illness (termed Legionnaires' disease) occurred at a state convention of the American Legion in Philadelphia, Pa., which resulted in 29 deaths. What is now known as *L. pneumophila* serotype 1 was originally isolated by standard techniques for the isolation of rickettsiae and subsequently shown to be the etiological agent for Legion-naires' disease, a form of atypical pneumonia with other non-respiratory complications. Since that first outbreak, Legionellae have been implicated in Pontiac fever and Pittsburgh pneumonia. Pontiac fever is a non-pneumonic febrile self-limiting illness caused by *L. pneumophila*. Pittsburgh pneumonia is a pulmonary legionellosis caused by *L. micdadei*.

Legionellae are gram negative, aerobic, facultative intracellular, parasitic bacteria found to be practically ubiquitous in fresh water supplies (including evaporative condensers, cooling towers, and potable water). It is believed that Legionellae cause disease when contaminated water is inhaled, often leading to epidemic or clustered outbreaks. In addition to community-acquired cases, legionellae may be a major cause of nosocomial infections. Along with hospitalization, host risk factors include smoking, advanced age, chronic lung disease, and immunosuppression.

The family Legionellaceae contains the single genus Legionella which includes some 29 species, 21 serogroups and 5 tentatively named species. According to DNA homology studies, *L. micdadei* is the most distant relative of *L. pneumophila*, and there is some who argue that *L. micdadei* should be properly classified as a member of the genus Tatlockia.

*L. pneumophila*, the primary cause of Legionnaire's disease, is the most common human isolate. The presence of legionellae in human clinical samples always provides clinically relevant information, as the bacteria are not considered normal human microflora.

Legionellae are slow growing organisms which are difficult to culture. Thus, isolation of *L. pneumophila* by laboratories can be difficult and time-consuming. Given the serious nature of the diseases, and the need to prescribe correct antibiotics, it is highly desirable for a physician to make a rapid and accurate diagnosis of the presence of these organisms. Current methods of detection of Legionellae include (a) culture; (b) direct fluorescence antibody (DFA); (c) nucleic acid probes for culture confirmation; and (d) serology (IFA). Serology is currently the most sensitive and specific test method. It is limited however, in that antibodies may persist in an individual's serum for years after infection.

Certain probes which are based on Legionella rRNAs are disclosed in WO 88/03957 "Nucleic Acid Probes for Detection and/or Quantification of Non-Viral Organisms", published Jun. 2, 1988, Applicant: Gen-Probe, Inventors: Hogan et al. This application however, discloses a mixture of three different probes which can be used to differentiate Legionella bacteria from non-Legionella bacteria. No probes suitable for solitary use are reported. It would be desirable to have probes which, when used singly or in pairs can be used in various diagnostic assays involving Legionella.

DESCRIPTION OF THE INVENTION

One aspect of this invention is to provide nucleic acids complementary to unique nucleic acid sequences within the ribosomal RNA (rRNA) of legionellae, and which can be used either singly or in pairs. It is a further aspect of the invention to provide for probes which either (1) specifically discriminate between *L. pneumophila* and other Legionelias; (2) specifically discriminate between a group of bacteria comprised of *L. pneumophila* and other species of Legionella (a Legionella cluster) and other bacteria; (3) specifically discriminate between *L. micdadei* and other Legionelias; or (4) specifically discriminate between Legionella and other genera.

Bacterial ribosomes contain three distinct RNA molecules which, at least in *Escherichia coli* are referred to as 5S, 16S, and 23S rRNAs. In eukaryotic organisms, there are four distinct rRNA species, generally referred to as 5S, 18S, 28S and 5.8S. These names are historically related to the size of the RNA molecules, as determined by their sedimentation rate. In actuality, however, rRNA molecules vary substantially in size between organisms. This notwithstanding, 5S, 16S and 23S rRNA are art-recognized names referring to rRNA molecules in any bacteria, including the legionellae and this convention will be used herein.

The probes of the present invention target either the 16S or the 23S rRNA molecules of various organisms of the genus Legionella.

Figure 1:
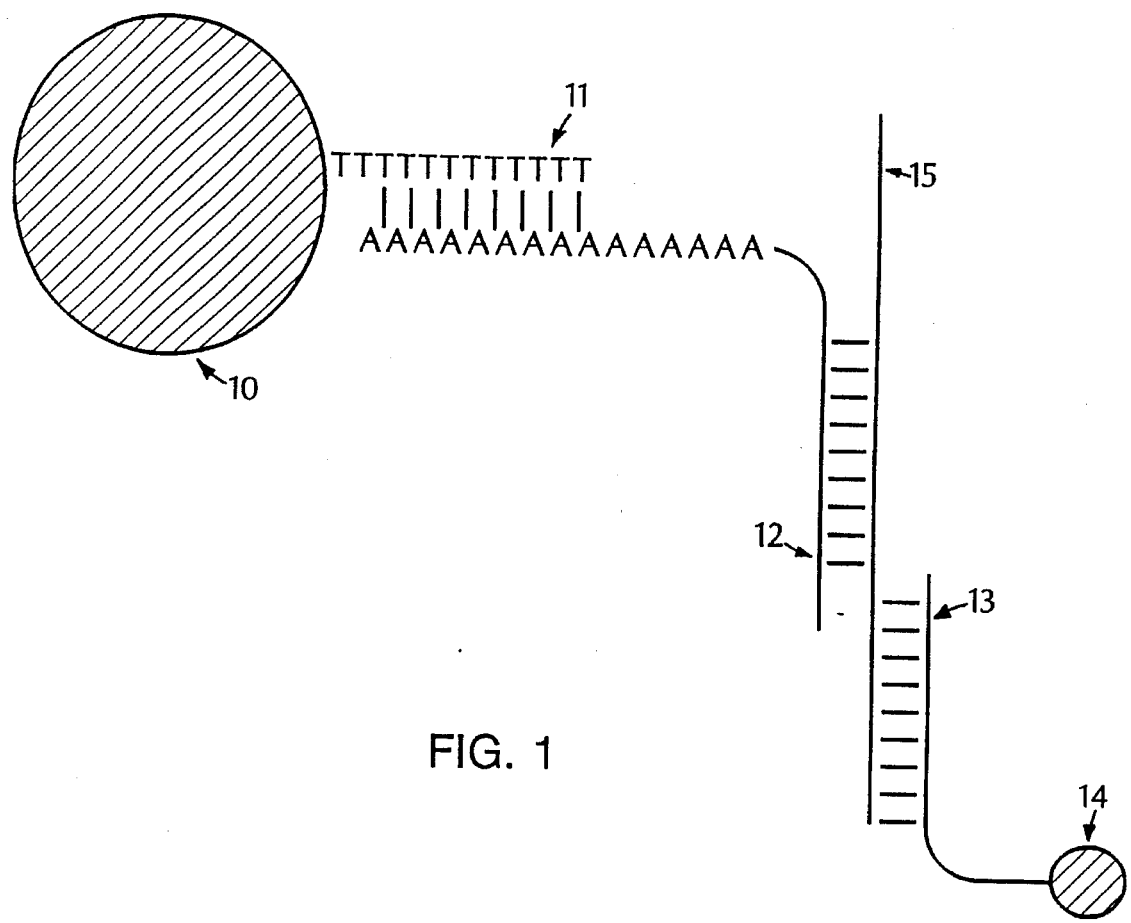
FIG. 1 is a diagram of a sandwich assay.

As used throughout the application and claims, the term "probe" will refer to synthetic or biologically produced nucleic acids, between 10 and 250 base pairs in length, which by design or selection, contain specific nucleotide sequences that allow specific and preferential hybridization under predetermined conditions to target nucleic acid sequences, and optionally contain a moiety for detection or for enhancing assay performance. A minimum of ten nucleotides is generally necessary in order to statistically obtain specificity and form stable hybridization products, and a maximum of 250 nucleotides generally represents an upper limit for sequences in which reaction parameters can be adjusted to determine mismatched sequences and preferential hybridization. Therefore, in general, a preferred length of a probe will be between 10 and 250 nucleotides. Probes may optionally contain certain constituents that pertain to their proper or optimal functioning under certain assay conditions. For example, probes may be modified to improve their resistance to nuclease degradation (such as by end-capping), to carry detection ligands (such as fluorescein, $^{32}$p, biotin, etc.) or to facilitate their capture onto a solid support (e.g. poly-deoxyadenosine "tails").

"Preferential hybridization" or "hybridizing preferentially" means that hybridization with the intended target nucleic acid results in a hybridization reaction product which is more stable than any hybridization reaction products resulting from hybridization with a non-target nucleic acid under identical conditions. It is well within the skill of the ordinary artisan to compare stability of hybridization reaction products and evaluate which one is more stable, i.e. determine which one has bound "preferentially".

As used herein, the terms "homology" and "homologous to" are meant to refer to the degree of similarity between two or more nucleic acid sequences, and is not meant to imply any taxonomic relatedness between organisms. The degree of similarity is expressed as a percentage, i.e. 90% homology between two sequences will mean that 90% of the bases of the first sequence are identically matched to the bases of the second sequence.

"Legionella cluster" means at least two members of the genus Legionella. Probes which identify a Legionella cluster will typically hybridize to rRNA of a plurality of Legionella species tested, (although not all Legionella).

"*L. pneumophila* cluster" means at least two strains of the species *L. pneumophila*. Probes which identify a *L. pneumophila* cluster will typically hybridize to rRNA of a plurality of *L. pneumophila* strains tested (although not all *L. pneumophila*).

"Specific" means that a nucleotide sequence will hybridize to a predetermined target sequence and will not substantially hybridize to a non-target sequence.

"Specifically discriminate" means that a probe will substantially hybridize to a predetermined target sequence and will not substantially hybridize to a non-target sequence.

"Hybridization" is a process by which, under predetermined reaction conditions, two partially or completely complementary strands of nucleic acid are allowed to come together in an antiparallel fashion to form a double stranded nucleic acid with specific and stable hydrogen bonds, following explicit rules pertaining to which nucleic acids bases may pair with one another.

"Substantial hybridization" means that the amount of hybridization observed will be such that one observing the results would consider the result positive in a clinical setting. Data which is considered "background noise" is not substantial hybridization.

"Stringent hybridization conditions" means approximately 35° C. to 65° C. in a salt solution of approximately 0.9 molar NaCl. Stringency may also be governed by such reaction parameters as the concentration and type of ionic species present in the hybridization solution, the types and concentrations of denaturing agents present, and the temperature of hybridization. Generally as hybridization conditions become more stringent, longer probes are preferred if stable hybrids are to be formed. As a rule, the stringency of the conditions under which a hybridization is to take place will dictate certain characteristics of the preferred probes to be employed. Such relationships are well understood and can be readily manipulated by those skilled in the art.

"Legionella sp." refers to any member of the genus Legionella, regardless of the species.

In accordance with this invention, there are provided nucleic acids having approximately 10 to 250 nucleotides which hybridize preferentially to rRNA or rDNA of a target organism selected from the group consisting of 1) *L. pneumophila,* 2) *L. micdadei,* 3) a Legionella cluster, or 4) a *L. pneumophila* cluster, or 5) all species of the genus Legionella. Under those same hybridization conditions, the nucleic acids of this invention do not substantially hybridize to the rRNA or rDNA of non-target organisms, or the host or environmental matrix which may be present in test samples.

Probes which specifically discriminate between *L. pneumophila* and other Legionella species are useful in the diagnosis of Legionnaires' disease or Pontiac fever. Probes which specifically discriminate between *L. micdadei* and other Legionella species are useful in the diagnosis of Pittsburgh pneumonia. Probes which specifically hybridize to a Legionella cluster are useful in detecting the presence of one or more organisms which makes up the particular cluster of bacteria. Probes which specifically discriminate between members of the genus Legionella and non-Legionella bacteria are useful in detecting the presence or absence of one or organisms belonging to the genus Legionella. Probes which specifically hybridize to a *L. pneumophila* cluster are useful in determining which strains (serotypes) of *L. pheumophila* are present. Probes which are either complementary to or at least 90% homologous to at least ten consecutive nucleic acids of the aforementioned nucleotides also form another aspect of this invention.

One embodiment of the nucleic acids and probes of this invention are those which are complementary to, at least 90% homologous with, or hybridize preferentially with regions of 16S rRNA or rDNA of either 1) *L. pneumophila,* 2) *L. micdadei,* 3) a Legionella cluster, 4) a *L. pneumophila* cluster, or 5) all Legionella species. The regions of 16S rRNA of particular interest include those indicated below. The numbering of these regions is by reference to the numbering used for *E. coli* rRNA designations.

*L. pneumophila* 16S rRNA positions 60 to 110, 1105 to 1165, and 1250 to 1315;

*L. micdadei* 16S rRNA positions 60 to 110, and 815 to 875;

Legionella sp. 16S rRNA positions 205 to 255, 425 to 475, 715 to 765, and 845 to 895 (for Legionella cluster probes);

Legionella sp. 120 to 175, and 800 to 870 (for Legionella genus probes).

Another embodiment of this invention includes nucleic acids and probes which are complementary to, at least 90% homologous with, or hybridize preferentially with regions of 23S rRNA or rDNA of either 1) a *L. pneumophila* cluster, 2) *L. micdadei,* 3) a Legionella cluster, or 4) all Legionella species. The regions of 23S rRNA of particular interest include:

*L. micdadei* 23S rRNA positions 285 to 335, 1195 to 1245, 1485 to 1565, and 1705 to 1755.

Legionella sp. 23S rRNA positions 285 to 335, 1485 to 1560 and 1705 to 1755 (for Legionella cluster probes)

Legionella sp. 23S rRNA positions 1565 to 1615 and 2270 to 2310 (for Legionella genus probes).

Preferably the nucleic acid composition is complementary to or homologous with at least 90% of a sequence comprising any ten consecutive nucleotides within sequences selected from the group of sequences defined by the group of probes consisting of: 2701, 2703, 2704, 2705, 2697, 2690, 2698, 2695, 2696, 2693, 2708, 2699, 2924, 2926, 2930, 2932, 2956, 2958, 2963, 2968, 2928, 2957, 2927, 2929, 2954, 2955, and 2959. The sequences of these probes are presented below.

A further embodiment of this invention includes a kit for the detection of either 1) *L. pneumophila,* 2) *L. micdadei,* 3) a Legionella cluster, 4) a *L. pheumophila* cluster, or 5) any Legionella species. The kit comprises a set of nucleic acids comprising at least two nucleic acids. Each nucleic acid is 10 to 250 nucleotides in length and is of a different base sequence composition. Each nucleic acid is complementary to or homologous with at least 90% of a sequence comprising any ten consecutive nucleotides selected from the group of sequences defined by probes 2701, 2703, 2704, 2705, 2697, 2690, 2698, 2695, 2696, 2693, 2708, 2699, 2924, 2926, 2930, 2932, 2956, 2958, 2963, 2968, 2928, 2957, 2927, 2929, 2954, 2955, and 2959. A set of nucleic acids particularly suited for detecting Legionella is a two-probe sandwich assay. The kit additionally comprises reagents, compositions, instructions, disposable hardware and suitable packaging to allow marketing in a convenient assembly.

A further embodiment of the present invention includes methods for the detection of the presence of 1) L. pneumophila, 2) L. micdadei, 3) a Legionella cluster, 4) a L. pneumophila cluster, or 5) any Legionella species. The method comprises the steps of contacting a sample suspected of containing a target with at least one nucleic acid. The nucleic acid has approximately 10 to 250 nucleotides which hybridize preferentially to 1) L. pneumophila, 2) L. micdadei, 3) a Legionella cluster, 4) a L. pneumophila cluster, or 5) any Legionella species rRNA or rDNA. The method includes the step of imposing hybridization conditions on the sample such that the nucleic acid binds preferentially to the target rRNA or rDNA to form nucleic acid complexes and detecting the complexes as an indication of the presence of the target organism(s). Preferably, the nucleic acid of the present invention is at least 90% homologous to a sequence comprising any ten consecutive nucleotides selected from the group consisting of sequences defined by probes 2701, 2703, 2704, 2705, 2697, 2690, 2698, 2695, 2696, 2693, 2708, 2699, 2924, 2926, 2930, 2932, 2956, 2958, 2963, 2968, 2928, 2957, 2927, 2929, 2954, 2955, and 2959.

The probes of the present invention provide the basis for development of a nucleic acid hybridization assay for the specific detection of legionellosis or its etiological agent in environmental samples such as water samples and clinical samples such as sputum, throat swabs, blood, urine, cerebrospinal fluid, skin, biopsy, saliva, synovial fluid, bronchial wash, bronchial lavage, or other tissue or fluid samples from human patient or veterinary subjects. The probes of the present invention also form the basis for confirmation of the presence or absence of 1) L. pneumophila, 2) L. micdadei, 3) a L. pneumophila cluster, 4) a L. pneumophila cluster, or 5) all Legionella species.

The first step taken in the development of the probes of the present invention involved the identification of the regions of 16S or 23S rRNA which potentially could serve as target sites for specific nucleic acid probes with the desired sensitivity. This included discovering which probe target sites were unique to L. pneumophila and L. micdadei, and discovering probe sites which were common to Legionella.

To accomplish the above analysis, precise alignments of legionellae 16S and 23S rRNA sequences were developed. The essentially complete 16S and 23S rRNA sequences of both L. pneumophila and L. micdadei were determined using standard laboratory protocols. The rDNAs so obtained were cloned into plasmid vectors from products produced by enzymic amplification (such as that described in Weisburg, 1991, J. Bacteriol. 173:697–703, which is incorporated herein by reference). The L. pneumophila and L. micdadei sequences were aligned with homologous sequences of other Legionella and non-Legionella rRNA sequences.

Based on the determined 16S and 23S RNA sequences of L. pneumophila and L. micdadei, various probes were designed, and synthesized. The specific behaviors of the probes are dependent to a significant extent on the assay format in which they are employed. Conversely, the assay format will dictate certain of the optimal features of the particular probes.

The discovery that a single probe or a pair of probes could be generated with the extraordinary inclusivity and exclusivity characteristics of the present invention with respect to 1) L. pneumophila, 2) L. micdadei, 3) a Legionella cluster, 4) a L. pneumophila cluster, or 5) any Legionella species without incurring undesirable levels of cross-reactivity was unpredictable and unexpected. Further, the finding that a single probe that has enough hybridization capability and selectivity for the target organism to be useful in a diagnostic assay was also unexpected.

A first group of preferred probes are able to differentiate between L. pneumophila and other Legionella species, and are useful in determining the presence of L. pneumophila in a sample. These probes hybridize preferentially only to L. pneumophila, and referred to as Probes 2704, 2705, 2708 and 2690. Probe 2957 gives somewhat weak hybridization signals, but is specific for *L. pneumophila.* Also given are two probes, 2929 and 2954 which only hybridize preferentially to some *L. pneumophila* strains tested, although they do not substantially hybridize to other organisms. These two probes, hereinafter called "*L. pneumophila* cluster" probes are useful in determining particular strains and/or serotypes.

*L. pneumophila* 16S rRNA Probes

*L. pneumophila* Probe 2704 (31mer 48% G + C) (SEQ ID NO:1)
5'-TCG CCA TCT GTC TAG CAA GCT AGA CAA TGC T-3'
*L. pneumophila* Probe 2705 (30mer 50% G + C) (SEQ ID NO:2)
5'-ACT TTT AAG GAT TTG CTC CAG GTC GCC CCT-3'
*L. pneumophila* Probe 2708 (31mer 45% G + C) (SEQ ID NO:3)
5'-ACT ACG ACC GAC TTT TAA GGA TTT GCT CCA G-3'
*L. pneumophila* Probe 2690 (36mer 50% G + C) (SEQ ID NO:4)
5'-TAG AGT CCC CAC CAT CAC ATG CTG GCA ACT AAG GAT-3'

*L. pneumophila* 23S rRNA Probe

*L. pneumophila* Probe 2957 (36mer 42% G + C) (SEQ ID NO:5)
5'-TCA ATG ACT TCT CTA TAC CAA AAG GGT CAG AAC CAC-3'

*L. pneumophila* cluster 23S rRNA Probes

*L. pneumophila* cluster Probe 2929 (31mer 42% G + C) (SEQ ID NO:6)
5'-CTC TAT CGC CAA CTT TCC CAA ATT GTT CTA C-3'
*L. pneumophila* cluster Probe 2954 (31mer 48% G + C) (SEQ ID NO:7)
5'-GCA CCT CAG AGT TAT GGA AAA CCG GAT TTG C-3'

A second group of preferred probes are able to differentiate between *L. micdadei* and substantially all other Legionella species, as these probes are able to bind preferentially to *L. micdadei.* They are useful in determining the presence of *L. micdadei* in a sample, and are designated Probes 2699, 2703, 2932, 2956, 2958, 2963, and 2968.

Probe 2703 hybridizes to *L. micdadei* and *L. dumoffi,* but not to any other Legionella species, and may be used to detect the presence of either or both of these microorganisms.

L. micdadei 16S rRNA PROBES

L. micdadei Probe 2699 (34mer 41% G + C) (SEQ ID NO:8)
5'-TTC GTC ACT AAC CTC ATT CAT AAG GCC AAC AAC T-3'

L. micdadei 23S rRNA PROBES

L. micdadei Probe 2932 (31mer 48% G + C) (SEQ ID NO:9)
5'-CTG TAT CGT GGT ACT TCC CAG AAC CTT CTA C-3'
L. micdadei Probe 2956 (30mer 57% G + C) (SEQ ID NO:10)
5'-GCC CAC CTC TCA GTG AAC CTT CTT CAG CCT-3'
L. micdadei Probe 2958 (32mer 59% G + C) (SEQ ID NO:11)
5'-GCA CCT CAG CCT TAA CAA GGG GCC GGA TTT GC-3'
L. micdadei Probe 2963 (32mer 44% G + C) (SEQ ID NO:12)
5'-CCT CTT CAG CTC ATT AAG CAT GTC AAT TCA CC-3'
L. micdadei Probe 2968 (37mer 47% G + C) (SEQ ID NO:13)
5'-TCA ATG ACT TCT CCG CAC ACC GTA GTG TCA GAA CCA C-3'

L. micdadei and L. dumoffi 16S rRNA PROBE

L. micdadei and L. dumoffi Probe 2703 (31mer 52% G + C) (SEQ ID NO:14)
5'-TCG CCA CCC ATC TAG TAA ACT AGA CCG TGC T-3'

A third group of preferred probes hybridize preferentially with a cluster of Legionella species compared to other bacteria. These probes are useful in distinguishing between various Legionella bacteria and strains.

Probe 2697 hybridizes to all *L. pneumophila* and three other Legionella species.

Probe 2698 hybridizes preferentially with all Legionella except for *L. bozemanii*, where hybridization is weak. Some non-substantial hybridization was noted with *Enterobacter agglomerans* and *Coxiella burnetii*.

Probe 2693 hybridizes with all Legionella species except for *L. micdadei*; some hybridization with *Acholeplasma laidlawii* was noted, but this is believed to be the result of an error in experimental manipulation, so this observation is not considered to be determinative. This probe also hybridizes with *Pseudomonas aeruginosa*; minor amounts of hybridization were noted with *Actinobacillus actinomycetamcornitans* and *Alteromonas putrefaciens*, *Coxiella burnetii* and *Wolbachia persica*.

Probe 2928 hybridizes to all Legionella species, and to certain other bacterial species: *Hafnia alvei, Morganella morganii, Proteus mirabilis, Providencia alcalifaciens, Serratia marcescens, Yersinia enterocolitica, Y. pseudotuberculosis* and *Francisella tularensis*. Weak hybridization was noted with *Edwardsiella tarda* and *Enterobacter agglomerans*.

Probe 2927 hybridizes to all Legionella and *Acinetobacter calcoaceticus, Aeromonas sobria, Edwardsiella tarda, Vibrio parahaemolyticus, Yersinia enterocolitica*, and *Y. pseudotuberculosis*. Lesser hybridization is noted with *Hafnia alvei, Proteus mirabilis, Providencia alcalifaciens, Serratia marcescens*, and *Mycoplasma hominis*. Even less hybridization is observed with *Plesiomonas shigelloides, Salmonella typhimudum*, and *Corynebactedum glutamicum*.

Probe 2955 hybridizes to all Legionella (but not well with *L. micdadei* and *L. bozemanii*); it also hybridizes to *Neissedae gonorrhoeae* and to a much lesser extent, *N. meningitidis*.

Probe 2494 hybridizes preferentially with various Legionella species, but does not hybridize to non-Legionella species.

Probe 2959 hybridizes with a group of the *L. pneumophila* strains and also with *L. dumoffii* (and weakly with *L. gormanii*).

Legionella Cluster 16S rRNA PROBES

Legionella Cluster Probe 2697 (33mer 48% G + C) (SEQ ID NO:15)
5'-TTT CCC CAA GTT GTC CCC CTC TTC AAG GCA TAT-3'
Legionella Cluster Probe 2698 (33mer 48% G + C) (SEQ ID NO:16)
5'-TCT TAA CCT ATC AAC CCT CCT CCC CAC TGA AAG-3'
Legionella Cluster Probe 2693 (30mer 60% G + C) (SEQ ID NO:17)
5'-AGG CGG TCA ACT TAT CGC GTT TGC TGC GCC-3'

Legionella Cluster 23S rRNA PROBES

Legionella Cluster Probe 2928 (31mer 51% G + C) (SEQ ID NO:18)
5'-TAA GAC CAA CTT TCG TTC CTG CTC GAG CCG T-3'
Legionella Cluster Probe 2927 (30mer 47% G + C) (SEQ ID NO:19)
5'-TCA GAC TCG ATT TCT CTA CGG CTC CCT TAT-3'
Legionella Cluster Probe 2955 (30mer 50% G + C) (SEQ ID NO:20)
5'-GCA CAC TTC TCA ATG CAC CTT CAT CAG CCT-3'
Legionella Cluster Probe 2924 (31mer 42% G + C) (SEQ ID NO:21)
5'-CAC AGT CAT CAT CAA AGT CCA GTG CAA AAC T-3'
Legionella Cluster Probe 2959 (32mer 50% G + C) (SEQ ID NO:22)
5'-CCT CTC CAG CTC TGA AAG TAA ATC CCA TCA CC-3'

A fourth group of preferred probes is able to differentiate between Legionella and non-Legionella species. They hybridize preferentially with all Legionella species and do not substantially hybridize with non-Legionella species. These are referred to as Legionella genus probes.

Probe 2696 hybridizes with all Legionella except (*L. micdadei*), but hybridizes only weakly.

Legionella GENUS 23S rRNA PROBES

Legionella Genus Probe 2926 (31mer 58% G + C) (SEQ ID NO:23)
5'-TGT CCG ACC GTA CCG AGG GTA CCT TTG TGC T-3'
Legionella Genus Probe 2930 (33mer 55% G + C) (SEQ ID NO:24)
5'-CGG TAC GGT TCT CTG TAA GTT ATG GCT AGC GGC-3'

Legionella GENUS 16S rRNA PROBES

Legionella Genus Probe 2701 (32mer, 59% G + C) (SEQ ID NO:25)
5'-TCG GAC GCA GGC TAA TCT TAA AGC GCC AGG CC-3'
Legionella Genus Probe 2696 (34mer, 40% G + C) (SEQ ID NO:26)
5'-TTC ATA TGG CCA ACA GCT AGT TGA CAT CGT TTA C-3'
Legionella Genus Probe 2695 (30mer 57% G + C) (SEQ ID NO:27)
5'-TGT CAG TAT TAG GCC AGG TAG CCG CCT TCG-3'

The probes of the present invention may be used in a "sandwich" assay. As shown in FIG. 1, the "sandwich" assay involves the use of a pair of probes simultaneously. One probe, designated the "capture" probe 12 is a bifunctional nucleotide made by adding a homopolymeric 3' tail to a probe with preferably high target specificity. The tail will hybridize to the complementary homopolymer 11 on a solid surface 10, such as a glass bead or a filter disc. Hybridization of the capture probe 12 to its target 15, in this case Legionella rRNA, would complex the target 15 with the solid support 10. The detector probe 13, preferably with some degree of specificity, would be a part of a detection scheme which may use virtually any sort of detection moiety 14, including radioactivity, fluorescence, chemiluminescence, color or other detector moiety. The detector probe may be incorporated as an RNA sequence into an amplifiable Q-beta midivariant as described by Kramer and Lizardi, 1989 Nature 339, which is hereby incorporated by reference.

An environmental sample or clinical sample, such as a swab, sputum, or tissue is processed as to liberate the total nucleic acid content. The sample, putatively containing disrupted legionellae is incubated in the presence of a capture probe, detector probe, and magnetic particle beads which have been derivatized with oligo-deoxy Thymidine in a chaotropic buffer such as guanidinium isothiocyanate.

If target molecules (for example, Legionella sp. rRNAs) are present, a Bead-Capture Probe-Target-Detector Probe hybridization complex is formed. The presence of a magnet near the bottom of the reaction tube will cause the magnetic particle-hybridization complex to adhere to the side of the tube, enabling the removal of the sample matrix, unbound probe, and other constituents not hybridized. Repeated rehydration and denaturation of the Bead-Capture Probe-Target-Detector Probe complex would enable significant background reduction. The final detection may involve spotting the beads on a membrane and assaying by an appropriate method, such as autoradiography, if the detector probe was labelled with a radioisotope. Alternatively, the detector probe may be an amplifiable midivariant probe.

The following non-limiting Examples are presented to better illustrate the invention.

EXAMPLE 1

Dot-Blot Analysis of Probe Hybridization Behavior

Dot-blot analysis, in accordance with well-known procedures, involves immobilizing a nucleic acid or a population of nucleic acids on a filter such as nitrocellulose, nylon or other derivatized membranes which can readily be obtained commercially. Either DNA or RNA can be so immobilized and subsequently tested for hybridization under a variety of conditions (stringencies) with nucleotide sequences or probes of interest. Under stringent conditions, probes with nucleotide sequences with greater complementarity to the target will exhibit a higher level of hybridization than probes whose sequences have less homology.

Probes of the present invention are tested in a dot-blot. One hundred nanograms of RNA, is purified by phenol extraction and centrifugation through cesium trifluoroacetate gradients, denatured and spotted on a nylon membrane. Probes are isotopically labelled with the addition of a $^{32}P$-Phosphorous moiety to the 5' end of the oligonucleotide by the established polynucleotide kinase reaction. Hybridization of the probes takes place overnight at a temperature of 60° C. with 10 ml 6×SSPE, 0.3% SDS, and $10^7$ CPM Probe. Unhybridized probe is removed by washing with 0.5X SSC and 0.1% SDS at 60° C. for twenty minutes. The filters are then exposed to X-ray film at −70° C., and the intensity of the hybridization signals is evaluated after three hours of autoradiographic exposure.

The following is a summary of results.

TABLE 1

PROBES TARGETING 16S rRNA

| Probe 2701: | All Legionella species tested. |
| Probe 2696: | All Legionella species tested, but weakly to L. micdadei. |
| Probe 2698: | All Legionella species tested except L. bozemanii. |
| Probe 2695: | All Legionella species tested. |
| Probe 2693: | All Legionella species tested except L. micdadei. Hybridization to Acholeplasma laidlawii believed to be an error in experimental manipulation. |
| Probe 2699: | L. micdadei specific |
| Probe 2703: | L. micdadei and L. dumoffii |
| Probe 2704: | L. pneumophila specific (all serotypes tested). |
| Probe 2705: | L. pneumophila specific (all serotypes tested). |
| Probe 2708: | L. pneumophila specific (all serotypes tested). |
| Probe 2690: | L. pneumophila specific (all serotypes tested). |
| Probe 2697: | L. pneumophila and three other Legionella species. |

PROBES TARGETING 23S rRNA

| Probe 2924: | Sporadic hybridization within the genus. |
| Probe 2926: | All Legionella species tested. |
| Probe 2930: | All Legionella species tested. |
| Probe 2931: | All Legionella species tested. |
| Probe 2932: | L. micdadei specific. |
| Probe 2956: | L. micdadei specific. |
| Probe 2958: | L. micdadei specific. |
| Probe 2963: | L. micdadei specific, but weak hybridizations. |
| Probe 2968: | L. micdadei specific. |
| Probe 2928: | All Legionella and many other eubacteria. |
| Probe 2957: | L. pneumophila, very weak hybridization. |
| Probe 2927: | All Legionella and many other eubacteria. |
| Probe 2929: | A subset of L. pneumophila strains tested; interestingly only one of the serotype 1 strains was positive. |
| Probe 2954: | A subset of the L. pneumophila strains tested. |
| Probe 2955: | All legionellae except L. micdadei and L. bozemanii. Also hybridizes with Neisseriae. |

The data from the dot blot assay are presented below as TABLE 2. In this table, ++++ indicates the strongest signals observed; +++ indicates a strong signal was observed; ++ indicates a somewhat weaker, but definitely positive hybridization signal observed; + indicates a weak signal; +− indicates a very weak, virtually absent, barely detectable signal; − indicates no signal observed. If a probe binds strongly (either ++++ or +++) to at least one target, but only exhibits a weak hybridization (+ or +−) to a second target, the probe is considered to substantially hybridize only with the targets giving the ++++ or +++ results.

TABLE 2

| Genus species | strain | EXPERIMENTALLY DETERMINED PROBE HYBRIDIZATION | | | | |
|---|---|---|---|---|---|---|
| | | 2701 | 2696 | 2698 | 2695 | 2693 |
| *Legionella pneumophila* | 33152 | ++++ | + | ++++ | ++++ | ++++ |
| *Legionella pneumophila* | 33153 | ++++ | + | ++++ | ++++ | ++++ |
| *Legionella pneumophila* | 33154 | ++++ | + | ++++ | ++++ | ++++ |
| *Legionella pneumophila* | 33155 | ++++ | + | ++++ | ++++ | ++++ |
| *Legionella pneumophila* | 33156 | ++++ | + | ++++ | ++++ | ++++ |

TABLE 2-continued

EXPERIMENTALLY DETERMINED PROBE HYBRIDIZATION

| Genus species | strain | | | | | |
|---|---|---|---|---|---|---|
| Legionella pneumophila | 33216 | ++++ | + | ++++ | ++++ | ++++ |
| Legionella pneumophila | 33215 | ++++ | + | ++++ | ++++ | ++++ |
| Legionella pneumophila | 33823 | ++++ | + | ++++ | ++++ | ++++ |
| Legionella pneumophila | 35096 | ++++ | + | ++++ | ++++ | ++++ |
| Legionella bozemanii | 33217 | ++++ | + | + | ++++ | ++++ |
| Legionella dumoffii | 33279 | ++++ | + | ++++ | ++++ | ++++ |
| Legionella gormanii | 33297 | ++++ | + | ++++ | ++++ | ++++ |
| Legionella longbeachae | 33462 | ++++ | + | ++++ | ++++ | ++++ |
| Legionella longbeachae | 33484 | ++++ | + | ++++ | ++++ | ++++ |
| Legionella micdadei | 33204 | ++++ | − | ++++ | ++++ | − |
| Acholsplasma laidlawii | | − | − | − | − | ++++ |
| Acinetobacter calcoacaticus | GT0002 | − | − | − | − | − |
| Actinobacillus actinomycatamcomitans | 29522 | − | − | − | − | + |
| Aeromonas sobria | GT0007 | − | − | − | − | − |
| Alteromonas putrefacians | GT1945 | − | − | − | − | + |
| Citrobacter diversus | GT0030 | − | − | − | − | − |
| Citrobacter freundii | GT0687 | − | − | − | − | − |
| Edwardsiella tarda | GT0569 | − | − | − | − | − |
| Entarobactar agglomerans | GT3130 | − | − | +− | − | − |
| Escherichia coli | GT1592 | − | − | − | − | − |
| Escherichia coli | GT1659 | − | − | − | − | − |
| Haemophilus influenza | ATCC33391 | − | − | − | − | − |
| Haemophilus parainfluenza | NCTC7901 | − | − | − | − | − |
| Haemophilus pleuropneumoniae | 27088 | − | − | − | − | − |
| Hafnia alvei | GT0241 | − | − | − | − | − |
| Xlabsiella pneumoniae | GT1500 | − | − | − | − | − |
| Morganella morganii | 25830 | − | − | − | − | − |
| Pastaurella aerogenes | 27883 | − | − | − | − | − |
| Pastaurella pneumotropica | NCTC8141 | − | − | − | − | − |
| Plesiomonas shigelloides | 14029 | − | − | − | − | − |
| Proteus mirabilis | GT1496 | − | − | − | − | − |
| Providencia alcalifaciens | GT0371 | − | − | − | − | − |
| Salmonella typhimurium | GT0389 | − | − | − | − | − |
| Serratia marcascans | GT0392 | − | − | − | − | − |
| Shigella flexneri | 12022 | − | − | − | − | − |
| Pseudomonas aeruginosa | 27853 | − | − | − | − | ++++ |
| Vibrio parahaemolyticus | GT0568 | − | − | − | − | − |
| Xanthomonas maltophilia | GT0417 | − | − | − | − | − |
| Yersinia enterocolitica | GT0419 | − | − | − | − | − |
| Yersinia pseudotuberculosis | 29833 | − | − | − | − | − |
| Neisseria gonorrhoeae | GT0315 | − | − | − | − | − |
| Neisseria meningitidis | GT0349 | − | − | − | − | − |
| Agrobactarium tumefaciens | GT2021 | − | − | − | − | − |
| Desulfovibrio desulfuricans | ATCC7757 | − | − | − | − | − |
| Francisella tularensis | GT2172 | − | − | − | − | − |
| Campylobacter jejuni | 33560 | − | − | − | − | − |
| Bacillus subtilis | GT0804 | − | − | − | − | − |
| Clostridium perfringens | ATCC13124 | − | − | − | − | − |
| Mycoplasma pneumoniae | PI1428 | − | − | − | − | − |
| Mycoplasma hominis | PG-21 | − | − | − | − | − |
| Ureaplasma urealyticum | #8 | − | − | − | − | − |
| Mycoplasma genitalium | G-37 | − | − | − | − | − |
| Staphlyococcus aureus | GT2047 | − | − | − | − | − |
| Streptococcus pneumoniae | GT0408 | − | − | − | − | − |
| Streptococcus salivarius | GT0410 | − | − | − | − | − |
| Bifidobacterium dentium | GT0012 | − | − | − | − | − |
| Corynebactarium genitalium | G45 | − | − | − | − | − |
| Corynebactarium glutamicum | GT2120 | − | − | − | − | − |
| Corynebactarium pseudotuberculosis | GT2122 | − | − | − | − | − |
| Mycobactarium kansasii | | − | − | − | − | − |
| Mycobactarium tuberculosis | GT2487 | − | − | − | − | − |
| Mycobactarium avium | GT3246 | − | − | − | − | − |
| Spirochaeta aurantia | | − | − | − | − | − |
| Bactaroides fragilis | 25285 | − | − | − | − | − |
| Bactaroides fragilis | 29771 | − | − | − | − | − |
| Chlamydia pneumoniae (TWAR) | | − | − | −. | − | − |
| Normal Stool RNA | | − | − | − | − | − |
| Wheat Germ | | − | − | − | − | − |
| Normal Human DNA | Caski | − | − | − | − | − |
| Candida albicans | 11006 | − | − | − | − | − |
| Aspergillus flavus | 10124 | − | − | − | − | − |
| Blastomycas dermatidis | 60193 | − | − | − | − | − |
| Cryptococcus neoformans | 14116 | − | − | − | − | − |
| Saccharomyces carevisiae | 18824 | − | − | − | − | − |
| Coxiella burnetii | PCR | − | − | +− | − | +− |

TABLE 2-continued

EXPERIMENTALLY DETERMINED PROBE HYBRIDIZATION

| Genus species | strain | | | | | |
|---|---|---|---|---|---|---|
| Legionella pneumophila | PCR | ++++ | + | ++++ | ++++ | ++++ |
| Wolbachia persica | PCR | – | – | – | – | +– |
| | | | | 2699 | | 2703 |
| Legionella pneumophila | 33152 | | | – | | – |
| Legionella pneumophila | 33153 | | | – | | – |
| Legionella pneumophila | 33154 | | | – | | – |
| Legionella pneumophila | 33155 | | | – | | – |
| Legionella pneumophila | 33156 | | | – | | – |
| Legionella pneumophila | 33216 | | | – | | – |
| Legionella pneumophila | 33215 | | | – | | – |
| Legionella pneumophila | 33823 | | | – | | – |
| Legionella pneumophila | 35096 | | | – | | – |
| Legionella bozemanii | 33217 | | | – | | – |
| Legionella dumoffii | 33279 | | | – | | ++++ |
| Legionella gormanii | 33297 | | | – | | – |
| Legionella longbeachae | 33462 | | | – | | – |
| Legionella longbeachae | 33484 | | | – | | – |
| Legionella micdadei | 33204 | | | ++++ | | ++++ |
| Acholsplasma laidlawii | | | | – | | – |
| Acinetobacter calcoacaticus | GT0002 | | | – | | – |
| Actinobacillus actinomycatamcomitans | 29522 | | | – | | – |
| Aeromonas sobria | GT0007 | | | – | | – |
| Alteromonas putrefacians | GT1945 | | | – | | – |
| Citrobacter diversus | GT0030 | | | – | | – |
| Citrobacter freundii | GT0687 | | | – | | – |
| Edwardsiella tarda | GT0569 | | | – | | – |
| Entarobactar agglomerans | GT3130 | | | – | | – |
| Escherichia coli | GT1592 | | | – | | – |
| Escherichia coli | GT1659 | | | – | | – |
| Haemophilus influenza | ATCC33391 | | | – | | – |
| Haemophilus parainfluenza | NCTC7901 | | | – | | – |
| Haemophilus pleuropneumoniae | 27088 | | | – | | – |
| Hafnia alvei | GT0241 | | | – | | – |
| Xlabsiella pneumoniae | GT1500 | | | – | | – |
| Morganella morganii | 25830 | | | – | | – |
| Pastaurella aerogenes | 27883 | | | – | | – |
| Pastaurella pneumotropica | NCTC8141 | | | – | | – |
| Plesiomonas shigelloides | 14029 | | | – | | – |
| Proteus mirabilis | GT1496 | | | – | | – |
| Providencia alcalifaciens | GT0371 | | | – | | – |
| Salmonella typhimurium | GT0389 | | | – | | – |
| Serratia marcascans | GT0392 | | | – | | – |
| Shigella flexneri | 12022 | | | – | | – |
| Pseudomonas aeruginosa | 27853 | | | – | | – |
| Vibrio parahaemolyticus | GT0568 | | | – | | – |
| Xanthomonas maltophilia | GT0417 | | | – | | – |
| Yersinia enterocolitica | GT0419 | | | – | | – |
| Yersinia pseudotuberculosis | 29833 | | | – | | – |
| Neisseria gonorrhoeae | GT0315 | | | – | | – |
| Neisseria meningitidis | GT0349 | | | – | | – |
| Agrobacterium tumefaciens | GT2021 | | | – | | – |
| Desulfovibrio desulfuricans | ATCC7757 | | | – | | – |
| Francisella tularensis | GT2172 | | | – | | – |
| Campylobacter jejuni | 33560 | | | – | | – |
| Bacillus subtilis | GT0804 | | | – | | – |
| Clostridium perfringens | ATCC13124 | | | – | | – |
| Mycoplasma pneumoniae | PI1428 | | | – | | – |
| Mycoplasma hominis | PG-21 | | | – | | – |
| Ureaplasma urealyticum | serotype 8 | | | – | | – |
| Mycoplasma genitalium | G-37 | | | – | | – |
| Staphlyococcus aureus | GT2047 | | | – | | – |
| Streptococcus pneumoniae | GT0408 | | | – | | – |
| Streptococcus salivarius | GT0410 | | | – | | – |
| Bifidobacterium dentium | GT0012 | | | – | | – |
| Corynebacterium genitalium | G45 | | | – | | – |
| Corynebacterium glutamicum | GT2120 | | | – | | – |
| Corynebacterium pseudotuberculosis | GT2122 | | | – | | – |
| Mycobacterium kansasii | | | | – | | – |
| Mycobacterium tuberculosis | GT2487 | | | – | | – |
| Mycobacterium avium | GT3246 | | | – | | – |
| Spirochaeta aurantia | | | | – | | – |
| Bactaroides fragilis | 25285 | | | – | | – |
| Bactaroides fragilis | 29771 | | | – | | – |

TABLE 2-continued

EXPERIMENTALLY DETERMINED PROBE HYBRIDIZATION

| Genus species | strain | | | | | |
|---|---|---|---|---|---|---|
| Chlamydia pneumoniae (TWAR) | | - | - | | | |
| Normal Stool RNA | | - | - | | | |
| Wheat Germ | | - | - | | | |
| Normal Human DNA | Caski | - | - | | | |
| Candida albicans | 11006 | - | - | | | |
| Aspergillus flavus | 10124 | - | - | | | |
| Blastomycas dermatidis | 60193 | - | - | | | |
| Cryptococcus neoformans | 14116 | - | - | | | |
| Saccharomyces carevisiae | 18824 | - | - | | | |
| Coxiella burnetii | PCR | - | - | | | |
| Legionella pneumophila | PCR | - | - | | | |
| Wolbachia persica | PCR | - | - | | | |
| | | 2704 | 2705 | 2708 | 2690 | 2697 |
| Legionella pneumophila serotype1 | 33152 | ++ | ++++ | ++++ | ++++ | ++++ |
| Legionella pneumophila serotype1 | 33153 | ++ | ++++ | ++++ | ++++ | ++++ |
| Legionella pneumophila serotype2 | 33154 | +++ | ++++ | ++++ | ++++ | ++++ |
| Legionella pneumophila serotype3 | 33155 | ++++ | ++++ | ++++ | ++++ | ++++ |
| Legionella pneumophila serotype4 | 33156 | ++++ | ++++ | ++++ | ++++ | ++++ |
| Legionella pneumophila serotype5 | 33216 | ++++ | ++++ | ++++ | ++++ | ++++ |
| Legionella pneumophila serotype6 | 33215 | ++++ | ++++ | ++++ | +++ | ++++ |
| Legionella pneumophila serotype7 | 33823 | ++++ | ++++ | ++++ | +++ | ++++ |
| Legionella pneumophila serotype8 | 35096 | ++++ | ++++ | ++++ | +++ | ++++ |
| Legionella bozemanii | 33217 | - | - | - | - | ++++ |
| Legionella dumoffii | 33279 | - | - | - | - | ++++ |
| Legionella gormanii | 33297 | - | - | - | - | ++++ |
| Legionella longbeachae serotype1 | 33462 | - | - | - | - | - |
| Legionella longbeachae serotype2 | 33484 | - | - | - | - | - |
| Legionella micdadei | 33204 | - | - | - | - | - |
| Acholsplasma laidlawii | | - | - | - | - | - |
| Acinetobacter calcoacaticus | GT0002 | - | - | - | - | - |
| Actinobacillus actinomycatamcomitans | 29522 | - | - | - | - | - |
| Aeromonas sobria | GT0007 | - | - | - | - | - |
| Alteromonas putrefacians | GT1945 | - | - | - | - | - |
| Citrobacter diversus | GT0030 | - | - | - | - | - |
| Citrobacter freundii | GT0687 | - | - | - | - | - |
| Edwardsiella tarda | GT0569 | - | - | - | - | - |
| Entarobactar agglomerans | GT3130 | - | - | - | - | - |
| Escherichia coli | GT1592 | - | - | - | - | - |
| Escherichia coli | GT1659 | - | - | - | - | - |
| Haemophilus influenza | ATCC33391 | - | - | - | - | - |
| Haemophilus parainfluenza | NCTC7901 | - | - | - | - | - |
| Haemophilus pleuropneumoniae | 27088 | - | - | - | - | - |
| Hafnia alvei | GT0241 | - | - | - | - | - |
| Xlabsiella pneumoniae | GT1500 | - | - | - | - | - |
| Morganella morganii | 25830 | - | - | - | - | - |
| Pastaurella aerogenes | 27883 | - | - | - | - | - |
| Pastaurella pneumotropica | NCTC8141 | - | - | - | - | - |
| Plesiomonas shigelloides | 14029 | - | - | - | - | - |
| Proteus mirabilis | GT1496 | - | - | - | - | - |
| Providencia alcalifaciens | GT0371 | - | - | - | - | - |
| Salmonella typhimurium | GT0389 | - | - | - | - | - |
| Serratia marcascans | GT0392 | - | - | - | - | - |
| Shigella flexneri | 12022 | - | - | - | - | - |
| Pseudomonas aeruginosa | 27853 | - | - | - | - | - |
| Vibrio parahaemolyticus | GT0568 | - | - | - | - | - |
| Xanthomonas maltophilia | GT0417 | - | - | - | - | - |
| Yersinia enterocolitica | GT0419 | - | - | - | - | - |
| Yersinia pseudotuberculosis | 29833 | - | - | - | - | - |
| Neisseria gonorrhoeae | GT0315 | - | - | - | - | - |
| Neisseria meningitidis | GT0349 | - | - | - | - | - |
| Agrobactarium tumefaciens | GT2021 | - | - | - | - | - |
| Desulfovibrio desulfuricans | ATCC7757 | - | - | - | - | - |
| Francisella tularensis | GT2172 | - | - | - | - | - |
| Campylobacter jejuni | 33560 | - | - | - | - | - |
| Bacillus subtilis | GT0804 | - | - | - | - | - |
| Clostridium perfringens | ATCC13124 | - | - | - | - | - |
| Mycoplasma pneumoniae | PI1428 | - | - | - | - | - |
| Mycoplasma hominis | PG-21 | - | - | - | - | - |
| Ureaplasma urealyticum | #8 | - | - | - | - | - |
| Mycoplasma genitalium | G-37 | - | - | - | - | - |
| Staphlyococcus aureus | GT2047 | - | - | - | - | - |
| Streptococcus pneumoniae | GT0408 | - | - | - | - | - |
| Streptococcus salivarius | GT0410 | - | - | - | - | - |

TABLE 2-continued

EXPERIMENTALLY DETERMINED PROBE HYBRIDIZATION

| Genus species | strain | | | | | |
|---|---|---|---|---|---|---|
| *Bifidobacterium dentium* | GT0012 | − | − | − | − | − |
| *Corynebacterium genitalium* | GT45 | − | − | − | +− | − |
| *Corynebacterium glutamicum* | GT2120 | − | − | − | − | − |
| *Corynebacterium pseudotuberculosis* | GT2122 | − | − | − | − | − |
| *Mycobacterium kansasii* | | − | − | − | − | − |
| *Mycobacterium tuberculosis* | GT2487 | − | − | − | +− | − |
| *Mycobacterium avium* | GT3246 | − | − | − | − | − |
| *Spirochaeta aurantia* | | − | − | − | − | − |
| *Bactaroides fragilis* | 25285 | − | − | − | − | − |
| *Bactaroides fragilis* | 29771 | − | − | − | − | − |
| *Chlamydia pneumoniae* (TWAR) | | − | − | − | − | − |
| Normal Stool RNA | | − | − | − | − | − |
| Wheat Germ | | − | − | − | − | − |
| Normal Human DNA | Caski | − | − | − | − | − |
| *Candida albicans* | 11006 | − | − | − | − | − |
| *Aspergillus flavus* | 10124 | − | − | − | − | − |
| *Blastomycas dermatidis* | 60193 | − | − | − | − | − |
| *Cryptococcus neoformans* | 14116 | − | − | − | − | − |
| *Saccharomyces carevisiae* | 18824 | − | − | − | − | − |
| *Coxiella burnetii* | PCR | − | +− | − | +− | − |
| *Legionella pneumophila* | PCR | ++++ | ++++ | ++++ | ++++ | ++++ |
| *Wolbachia persica* | PCR | − | − | − | +− | − |

| | | 2924 | 2926 | 2930 |
|---|---|---|---|---|
| *Legionella pneumophila* serotype1 | 33152 | ++ | ++++ | ++++ |
| *Legionella pneumophila* serotype1 | 33153 | +++ | ++++ | ++++ |
| *Legionella pneumophila* serotype2 | 33154 | +++ | ++++ | ++++ |
| *Legionella pneumophila* serotype3 | 33155 | ++ | ++++ | +++ |
| *Legionella pneumophila* serotype4 | 33156 | +++ | ++++ | ++++ |
| *Legionella pneumophila* serotype5 | 33216 | +++ | ++++ | +++ |
| *Legionella pneumophila* serotype6 | 33215 | +++ | ++++ | ++++ |
| *Legionella pneumophila* serotype7 | 33823 | +++ | ++++ | ++++ |
| *Legionella pneumophila* serotype8 | 35096 | + | ++++ | ++++ |
| *Legionella bozemanii* | 33217 | + | ++++ | ++++ |
| *Legionella dumoffii* | 33279 | + | ++++ | ++++ |
| *Legionella gormanii* | 33297 | + | ++++ | ++++ |
| *Legionella longbeachae* serotype1 | 33462 | ++ | ++++ | ++++ |
| *Legionella longbeachae* serotype2 | 33484 | ++ | ++++ | ++++ |
| *Legionella micdadei* | 33204 | +++ | ++++ | ++++ |
| *Legionella jordanis* | | + | ++++ | ++ |
| *Acholsplasma laidlawii* | | − | − | − |
| *Acinetobacter calcoaticus* | GT0002 | − | − | − |
| *Actinobacillus actinomycatamcomitans* | 29522 | − | − | − |
| *Aeromonas sobria* | GT0007 | − | − | − |
| *Alteromonas putrefacians* | GT1945 | − | − | − |
| *Citrobacter diversus* | GT0030 | − | − | − |
| *Citrobacter freundii* | GT0687 | − | − | − |
| *Edwardsiella tarda* | GT0569 | − | − | − |
| *Entarobactar agglomerans* | GT3130 | − | − | − |
| *Escherichia coli* | GT1592 | − | − | − |
| *Escherichia coli* | GT1659 | − | − | − |
| *Haemophilus influenza* | ATCC33391 | − | − | − |
| *Haemophilus parainfluenza* | NCTC7901 | − | − | − |
| *Haemophilus pleuropneumoniae* | 27088 | − | − | − |
| *Hafnia alvei* | GT0241 | − | − | − |
| *Xlabsiella pneumoniae* | GT1500 | − | − | − |
| *Morganella morganii* | 25830 | − | − | − |
| *Pastaurella aerogenes* | 27883 | − | − | − |
| *Pastaurella pneumotropica* | NCTC8141 | − | − | − |
| *Plesiomonas shigelloides* | 14029 | − | − | − |
| *Proteus mirabilis* | GT1496 | − | − | − |
| *Providencia alcalifaciens* | GT0371 | − | − | − |
| *Salmonella typhimurium* | GT0389 | − | − | − |
| *Serratia marcascans* | GT0392 | − | − | − |
| *Shigella flexneri* | 12022 | − | − | − |
| *Pseudomonas aeruginosa* | 27853 | − | − | − |
| *Vibrio parahaemolyticus* | GT0568 | − | − | − |
| *Xanthomonas maltophilia* | GT0417 | − | − | − |
| *Yersinia enterocolitica* | GT0419 | − | − | − |
| *Yersinia pseudotuberculosis* | 29833 | − | − | − |
| *Neisseria gonorrhoeae* | GT0315 | − | − | − |
| *Neisseria meningitidis* | GT0349 | − | − | − |
| *Agrobacterium tumefaciens* | GT2021 | − | − | − |
| *Desulfovibrio desulfuricans* | ATCC7757 | − | − | − |

TABLE 2-continued

EXPERIMENTALLY DETERMINED PROBE HYBRIDIZATION

| Genus species | strain | | | |
|---|---|---|---|---|
| *Francisella tularensis* | GT2172 | − | + | − |
| *Campylobacter jejuni* | 33560 | − | − | − |
| *Bacillus subtilis* | GT0804 | − | − | − |
| *Clostridium perfringens* | ATCC13124 | − | − | − |
| *Mycoplasma pneumoniae* | PI1428 | − | − | − |
| *Mycoplasma hominis* | PG-21 | − | − | − |
| *Ureaplasma urealyticum* | #8 | − | − | − |
| *Mycoplasma genitalium* | G-37 | − | − | − |
| *Staphlyococcus aureus* | GT2047 | − | − | − |
| *Streptococcus pneumoniae* | GT0408 | − | − | − |
| *Streptococcus salivarius* | GT0410 | − | − | − |
| *Bifidobactarium dentium* | GT0012 | − | − | − |
| *Corynebacterium genitalium* | GT45 | − | − | − |
| *Corynebacterium glutamicum* | GT2120 | − | − | − |
| *Corynebacterium pseudotuberculosis* | GT2122 | − | − | − |
| *Mycobacterium kansasii* | | − | − | − |
| *Mycobacterium tuberculosis* | GT2487 | − | − | − |
| *Mycobacterium avium* | GT3246 | − | − | − |
| *Spirochaeta aurantia* | | | | |
| *Bactaroides fragilis* | 25285 | − | − | − |
| *Bactaroides fragilis* | 29771 | − | − | − |
| *Chlamydia pneumoniae* (TWAR) | | − | − | − |
| Normal Stool RNA | | − | − | − |
| Wheat Germ | | − | − | − |
| Normal Human DNA | Caski | − | − | − |
| *Candida albicans* | 11006 | − | − | − |
| *Aspergillus flavus* | 10124 | − | − | − |
| *Blastomycas dermatidis* | 60193 | − | − | − |
| *Cryptococcus neoformans* | 14116 | − | − | − |
| *Saccharomyces carevisiae* | 18824 | − | − | − |

| | | 2932 | 2956 | 2958 | 2963 | 2968 |
|---|---|---|---|---|---|---|
| *Legionella pneumophila* serotype1 | 33152 | − | − | − | − | − |
| *Legionella pneumophila* serotype1 | 33153 | − | − | − | − | − |
| *Legionella pneumophila* serotype2 | 33154 | − | − | − | − | − |
| *Legionella pneumophila* serotype3 | 33155 | − | − | − | − | − |
| *Legionella pneumophila* serotype4 | 33156 | − | − | − | − | − |
| *Legionella pneumophila* serotype5 | 33216 | − | − | − | − | − |
| *Legionella pneumophila* serotype6 | 33215 | − | − | − | − | − |
| *Legionella pneumophila* serotype7 | 33823 | − | − | − | − | − |
| *Legionella pneumophila* serotype8 | 35096 | − | − | − | − | − |
| *Legionella bozemanii* | 33217 | − | − | − | − | − |
| *Legionella dumoffii* | 33279 | − | − | − | − | − |
| *Legionella gormanii* | 33297 | − | − | − | − | − |
| *Legionella longbeachae* serotype1 | 33462 | − | − | − | − | − |
| *Legionella longbeachae* serotype2 | 33484 | − | − | − | − | − |
| *Legionella micdadei* | 33204 | ++++ | ++++ | ++++ | ++ | ++++ |
| *Legionella jordania* | | − | − | − | − | − |
| *Acholsplasma laidlawii* | | − | − | − | − | − |
| *Acinetobacter calcoacaticus* | GT0002 | − | − | − | − | − |
| *Actinobacillus actinomycatamcomitans* | 29522 | − | − | − | − | − |
| *Aeromonas sobria* | GT0007 | − | − | − | − | − |
| *Alteromonas putrefacians* | GT1945 | − | − | − | − | − |
| *Citrobacter diversus* | GT0030 | − | − | − | − | − |
| *Citrobacter freundii* | GT0687 | − | − | − | − | − |
| *Edwardsiella tarda* | GT0569 | − | − | − | − | − |
| *Entarobactar agglomerans* | GT3130 | − | − | − | − | − |
| *Escherichia coli* | GT1592 | − | − | − | − | − |
| *Escherichia coli* | GT1659 | − | − | − | − | − |
| *Haemophilus influenza* | ATCC33391 | − | + | − | − | − |
| *Haemophilus parainfluenza* | NCTC7901 | − | − | − | − | − |
| *Haemophilus pleuropneumoniae* | 27088 | − | − | − | − | − |
| *Hafnia alvei* | GT0241 | − | − | − | − | − |
| *Xlabsiella pneumoniae* | GT1500 | − | − | − | − | − |
| *Morganella morganii* | 25830 | − | − | − | − | − |
| *Pastaurella aerogenes* | 27883 | − | − | − | − | − |
| *Pastaurella pneumotropica* | NCTC8141 | − | − | − | − | − |
| *Plesiomonas shigelloides* | 14029 | − | − | − | − | − |
| *Proteus mirabilis* | GT1496 | − | − | − | − | − |
| *Providencia alcalifaciens* | GT0371 | − | − | − | − | − |
| *Salmonella typhimurium* | GT0389 | − | − | − | − | − |
| *Serratia marcascans* | GT0392 | − | − | − | − | − |
| *Shigella flexneri* | 12022 | − | − | − | − | − |
| *Pseudomonas aeruginosa* | 27853 | − | − | − | − | − |

TABLE 2-continued

EXPERIMENTALLY DETERMINED PROBE HYBRIDIZATION

| Genus species | strain | | | | | | |
|---|---|---|---|---|---|---|---|
| *Vibrio parahaemolyticus* | GT0568 | − | − | − | − | − | − |
| *Xanthomonas maltophilia* | GT0417 | − | − | − | − | − | − |
| *Yersinia enterocolitica* | GT0419 | − | − | − | − | − | − |
| *Yersinia pseudotuberculosis* | 29833 | − | − | − | − | − | − |
| *Neisseria gonorrhoeae* | GT0315 | − | − | − | − | − | − |
| *Neisseria meningitidis* | GT0349 | − | − | − | − | − | − |
| *Agrobactarium tumefaciens* | GT2021 | − | − | − | − | − | − |
| *Desulfovibrio desulfuricans* | ATCC7757 | − | − | − | − | − | − |
| *Francisella tularensis* | GT2172 | − | − | − | − | − | − |
| *Campylobacter jejuni* | 33560 | − | − | − | − | − | − |
| *Bacillus subtilis* | GT0804 | − | − | − | − | − | − |
| *Clostridium perfringens* | ATCC13124 | − | − | − | − | − | − |
| *Mycoplasma pneumoniae* | PI1428 | − | − | − | − | − | − |
| *Mycoplasma hominis* | PG-21 | − | − | − | − | − | − |
| *Ureaplasma urealyticum* | #8 | − | − | − | − | − | − |
| *Mycoplasma genitalium* | G-37 | − | − | − | − | − | − |
| *Staphlyococcus aureus* | GT2047 | − | − | − | − | − | − |
| *Streptococcus pneumoniae* | GT0408 | − | − | − | − | − | − |
| *Streptococcus salivarius* | GT0410 | − | − | − | − | − | − |
| *Bifidobacterium dentium* | GT0012 | − | − | − | − | − | − |
| *Corynebactarium genitalium* | GT45 | − | − | − | − | − | − |
| *Corynebactarium glutamicum* | GT2120 | − | − | − | − | − | − |
| *Corynebactarium pseudotuberculosis* | GT2122 | − | − | − | − | − | − |
| *Mycobactarium kansasii* | | − | − | − | − | − | − |
| *Mycobactarium tuberculosis* | GT2487 | − | − | − | − | − | − |
| *Mycobactarium avium* | GT3246 | − | − | − | − | − | − |
| *Spirochaeta aurantia* | | − | − | − | − | − | − |
| *Bactaroides fragilis* | 25285 | − | − | − | − | − | − |
| *Bactaroides fragilis* | 29771 | − | − | − | − | − | − |
| *Chlamydia pneumoniae* (TWAR) | | − | − | − | − | − | − |
| Normal Stool RNA | | − | − | − | − | − | − |
| Wheat Germ | | − | − | − | − | − | − |
| Normal Human DNA | Caski | − | − | − | − | − | − |
| *Candida albicans* | 11006 | − | − | − | − | − | − |
| *Aspergillus flavus* | 10124 | − | − | − | − | − | − |
| *Blastomyces dermatidis* | 60193 | − | − | − | − | − | − |
| *Cryptococcus neoformans* | 14116 | − | − | − | − | − | − |
| *Saccharomyces carevisiae* | 18824 | − | − | − | − | − | − |

| | | 2928 | 2957 | 2927 | 2929 | 2954 | 2955 | 2959 |
|---|---|---|---|---|---|---|---|---|
| *Legionella pneumophila* serotype1 | 33152 | ++++ | +− | ++++ | ++++ | ++++ | ++++ | ++++ |
| *Legionella pneumophila* serotype1 | 33153 | ++++ | +− | ++++ | +− | ++++ | ++++ | ++++ |
| *Legionella pneumophila* serotype2 | 33154 | ++++ | +− | ++++ | ++++ | ++++ | ++++ | ++++ |
| *Legionella pneumophila* serotype3 | 33155 | ++++ | +− | ++++ | +− | ++++ | ++++ | − |
| *Legionella pneumophila* serotype4 | 33156 | ++++ | +− | ++++ | − | + | ++++ | ++++ |
| *Legionella pneumophila* serotype5 | 33216 | ++++ | +− | ++++ | − | + | ++++ | ++++ |
| *Legionella pneumophila* serotype6 | 33215 | ++++ | +− | ++++ | ++++ | ++++ | ++++ | ++++ |
| *Legionella pneumophila* serotype7 | 33823 | ++++ | +− | ++++ | +− | ++++ | ++++ | − |
| *Legionella pneumophila* serotype8 | 35096 | ++++ | +− | ++++ | ++++ | ++++ | ++++ | ++++ |
| *Legionella bozemanii* | 33217 | ++++ | − | ++++ | − | − | +− | − |
| *Legionella dumoffii* | 33279 | +++ | − | ++++ | − | − | ++++ | ++++ |
| *Legionella gormanii* | 33297 | ++++ | − | ++++ | − | − | ++++ | +− |
| *Legionella longbeachae* serotype1 | 33462 | ++++ | − | ++++ | − | − | ++++ | − |
| *Legionella longbeachae* serotype2 | 33484 | ++++ | − | ++++ | − | − | ++++ | − |
| *Legionella micdadei* | 33204 | ++++ | − | ++++ | − | − | +− | − |
| *Legionella jordanis* | | +++ | − | ++++ | − | − | ++++ | − |
| *Acholsplasma laidlawii* | | − | − | − | − | − | − | − |
| *Acinetobacter calcoacaticus* | GT0002 | − | − | ++++ | − | − | − | − |
| *Actinobacillus actinomycatamcomitans* | 29522 | − | − | − | − | − | − | − |
| *Aeromonas sobria* | GT0007 | − | − | +++ | − | − | − | − |
| *Alteromonas putrefacians* | GT1945 | − | − | − | − | − | − | − |
| *Citrobacter diversus* | GT0030 | − | − | − | − | − | − | − |
| *Citrobacter freundii* | GT0687 | − | − | − | − | − | − | − |
| *Edwardsiella tarda* | GT0569 | + | − | +++ | − | − | − | − |
| *Entarobactar agglomerans* | GT3130 | +− | − | − | − | − | − | − |
| *Escherichia coli* | GT1592 | − | − | − | − | − | − | − |
| *Escherichia coli* | GT1659 | − | − | − | − | − | − | − |
| *Haemophilus influenza* | ATCC33391 | − | − | − | − | − | − | − |
| *Haemophilus parainfluenza* | NCTC7901 | − | − | − | − | − | − | − |
| *Haemophilus pleuropneumoniae* | 27088 | − | − | − | − | − | − | − |
| *Hafnia alvei* | GT0241 | ++++ | − | ++ | − | − | − | − |
| *Xlabsiella pneumoniae* | GT1500 | − | − | − | − | − | − | − |
| *Morganella morganii* | 25830 | ++++ | − | − | − | − | − | − |
| *Pastaurella aerogenes* | 27883 | − | − | − | − | − | − | − |

TABLE 2-continued

EXPERIMENTALLY DETERMINED PROBE HYBRIDIZATION

| Genus species | strain | | | | | | | |
|---|---|---|---|---|---|---|---|---|
| Pastaurella pneumotropica | NCTC8141 | − | − | − | − | − | − | − |
| Plesiomonas shigelloides | 14029 | − | − | + | − | − | − | − |
| Proteus mirabilis | GT1496 | ++++ | − | ++ | − | − | − | − |
| Providencia alcalifaciens | GT0371 | ++++ | − | ++ | − | − | − | − |
| Salmonella typhimurium | GT0389 | − | − | + | − | − | − | − |
| Serratia marcascans | GT0392 | ++++ | − | ++ | − | − | − | − |
| Shigella flexneri | 12022 | − | − | − | − | − | − | − |
| Pseudomonas aeruginosa | 27853 | − | − | − | − | − | − | − |
| Vibrio parahaemolyticus | GT0568 | − | − | +++ | − | − | − | − |
| Xanthomonas maltophilia | GT0417 | − | − | − | − | − | − | − |
| Yersinia enterocolitica | GT0419 | ++++ | − | +++ | − | − | − | − |
| Yersinia pseudotuberculosis | 29833 | ++++ | − | +++ | − | − | − | − |
| Neisseria gonorrhoeae | GT0315 | − | − | − | − | − | ++++ | − |
| Neisseria meningitidis | GT0349 | − | − | − | − | − | +− | − |
| Agrobactarium tumefaciens | GT2021 | − | − | − | − | − | − | − |
| Desulfovibrio desulfuricans | ATCC7757 | − | − | − | − | − | − | − |
| Francisella tularensis | GT2172 | ++++ | − | − | − | − | − | − |
| Campylobacter jejuni | 33560 | − | − | − | − | − | − | − |
| Bacillus subtilis | GT0804 | − | − | − | − | − | − | − |
| Clostridium perfringens | ATCC13124 | − | − | − | − | − | − | − |
| Mycoplasma pneumoniae | PI1428 | − | − | − | − | − | − | − |
| Mycoplasma hominis | PG-21 | − | − | ++ | − | − | − | − |
| Ureaplasma urealyticum | #8 | − | − | − | − | − | − | − |
| Mycoplasma genitalium | G-37 | − | − | − | − | − | − | − |
| Staphlyococcus aureus | GT2047 | − | − | − | − | − | − | − |
| Streptococcus pneumoniae | GT0408 | − | − | − | − | − | − | − |
| Streptococcus salivarius | GT0410 | − | − | − | − | − | − | − |
| Bifidobactarium dentium | GT0012 | − | − | − | − | − | − | − |
| Corynebactarium genitalium | GT45 | − | − | − | − | − | − | − |
| Corynebactarium glutamicum | GT2120 | − | − | +− | − | − | − | − |
| Corynebactarium pseudotuberculosis | GT2122 | − | − | − | − | − | − | − |
| Mycobactarium kansasii | | − | − | − | − | − | − | − |
| Mycobactarium tuberculosis | GT2487 | − | − | − | − | − | − | − |
| Mycobactarium avium | GT3246 | − | − | − | − | − | − | − |
| Spirochaeta aurantia | | − | − | − | − | − | − | − |
| Bactaroides fragilis | 25285 | − | − | − | − | − | − | − |
| Bactaroides fragilis | 29771 | − | − | − | − | − | − | − |
| Chlamydia pneumoniae (TWAR) | | − | − | − | − | − | − | − |
| Normal Stool RNA | | − | − | − | − | − | − | − |
| Wheat Germ | | − | − | − | − | − | − | − |
| Normal Human DNA | Caski | − | − | − | − | − | − | − |
| Candida albicans | 11006 | − | − | − | − | − | − | − |
| Aspergillus flavus | 10124 | − | − | − | − | − | − | − |
| Blastomycas dermatidis | 60193 | − | − | − | − | − | − | − |
| Cryptococcus neoformans | 14116 | − | − | − | − | − | − | − |
| Saccharomyces carevisae | 18824 | − | − | − | − | − | − | − |

HYBRIDIZATION = 10 ML of 6X SSPE, 0.3% SDS, 10E7 CPM PROBE, 60° C. OVERNIGHT
WASH = 0.5X SSC, 0.1% SDS AT 60° C. FOR 20 MIN.
EXPOSURE = X-RAY FILM −70° C. 3 HRS.

EXAMPLE 2

Dual Probe Hybridization

The following probe pairs are used in a sandwich assay:
Legionella genus 16S rRNA: Probe 2701+Probe 1660 (Probe 1660 will bind with all bacterial species tested to date. It is described in PCT application WO90/15157, which is hereby incorporated by reference).

| | Probe 2695 + Probe 2696 |
|---|---|
| L. pneumophila 16S rRNA: | Probe 2704 + Probe 2697 |
| | Probe 2705 + Probe 2690 |
| L. micdadei 23S rRNA: | Probe 2958 + 2968 |
| | Probe 2956 + 2958 |
| Legionella genus 23S rRNA: | Probe 2926 + Probe 2931 |
| L. micdadei 16S rRNA: | Probe 2699 + Probe 2695 |

In each instance, target organism was detected, and non-target DNA was not detected.

EXAMPLE 3

Clinical Diagnosis of Legionellosis

A sample from an individual suspected of having legionellosis is processed to yield DNA. A probe of this invention is used in conjunction with the antiparallel complement of a second probe of this invention to enzymatically amplify a segment of L. pneumophila or L. micadei gene encoding legionella rRNA in a polymerase chain reaction. Resultant material is then assayed in a sandwich assay. The polymerase chain reaction can, itself be made either highly specific by employing probe/primers described herein, or the reaction may be made more general using probes such as those described in copending U.S. Ser. No. 359,158 which is hereby incorporated by reference, and then identifying the amplification product as L. pneumophila using a sandwich assay.

EXAMPLE 4

In situ Hybridization as a Cytological Stain

The probes of this invention may be used as cytological staining reagents. A sample, such as a sputum sample is applied to a microscope slide. After fixation and lysis, hybridization of probes is carried out in situ. For example, Probe 2705 (hybridizes to all serotypes of *L. pneumophila*) is labelled with a florescent label and used to stain the specimen. If *L. pheumophila* is present in the sample, small fluorescent bodies will be visible under a fluorescent microscope.

EXAMPLE 5

Confirmation of Presence of Legionella sp. Following Culture

Following a standard cultivation step for Legionella, such as on buffered charcoal yeast extract agar plate or in liquid culture enrichment, the presence of Legionella is tested for. One method is by use of the sandwich assay described in Example 2. Pure culture is not necessary.

---

What is claimed is:

1. An isolated nucleic acid which hybridizes preferentially to 23S or 16S rRNA or rDNA of *Legionella pneumophila* bacteria and not to non-*Legionella pneumophila* organisms, wherein said nucleic acid is fully complementary or identical to a nucleotide sequence of one of probes 2704 (SEQ ID NO: 1), 2705 (SEQ ID NO: 2), 2708 (SEQ ID NO: 3), 2690 (SEQ ID NO: 4), 2957 (SEQ ID NO: 5), 2929 (SEQ ID NO: 6), or 2954 (SEQ ID NO: 7).

2. A probe comprising a nucleic acid of claim 1 and a detection or enhancement moiety.

3. A method of detecting the presence of *Legionella pneumophila* in a sample suspected of containing Legionella bacteria comprising a) contacting the sample with at least one isolated nucleic acid of claim 1, b) imposing hybridization conditions on the sample and said isolated nucleic acid to allow the formation of a hybridization product between said nucleic acid and rRNA or rDNA from *L. pneumophila* bacteria, if present in the sample, but not from rRNA or rDNA from non-*L. pneumophila* bacteria; and c) detecting the hybridization product as an indication of the presence of *L. pneumophila* in the sample.

4. An isolated nucleic acid which hybridizes preferentially to 23S or 16S rRNA or rDNA or *Legionella micdadei* bacteria and not to non-*Legionella micdadei* organisms, wherein said nucleic acid is fully complementary or identical to a nucleotide sequence of one of probes 2699 (SEQ ID NO: 8), 2932 (SEQ ID NO: 9), 2956 (SEQ ID NO: 10), 2958 (SEQ ID NO: 11), 2963 (SEQ ID NO: 12), or 2968 (SEQ ID NO: 13).

5. A probe comprising a nucleic acid of claim 4 and a detection or enhancement moiety.

6. A method of detecting the presence of *Legionella micdadei* in a sample suspected of containing Legionella bacteria comprising a) contacting the sample with at least one isolated nucleic acid of claim 4, b) imposing hybridization conditions on the sample and said isolated nucleic acid to allow the formation of a hybridization product between said nucleic acid and rRNA or rDNA from *L. micdadei* bacteria, if present in the sample, but not from rRNA or rDNA from non-*L. micdadei* bacteria; and c) detecting the hybridization product as an indication of the presence of *L. micdadei* in the sample.

7. An isolated nucleic acid which hybridizes preferentially to 23S or 16S rRNA or rDNA of Legionella bacteria and not to non-Legionella organisms, wherein said nucleic acid is fully complementary or identical to a nucleotide sequence of one of probes 2697 (SEQ ID NO: 15), 2698 (SEQ ID NO: 16), 2693 (SEQ ID NO: 17), 2959 (SEQ ID NO: 22), 2696 (SEQ ID NO: 26), 2701 (SEQ ID NO: 25), 2695 (SEQ ID NO: 27), or 2703 (SEQ ID NO: 14).

8. A probe comprising a nucleic acid of claim 7 and a detection or enhancement moiety.

9. A method of detecting the presence of Legionella bacteria in a sample suspected of containing Legionella bacteria comprising a) contacting the sample with at least one isolated nucleic acid of claim 7, b) imposing hybridization conditions on the sample and said isolated nucleic acid to allow the formation of a hybridization product between said nucleic acid and rRNA or rDNA from Legionella bacteria, if present in the sample, but not from rRNA or rDNA from non-Legionella bacteria; and c) detecting the hybridization product as an indication of the presence of Legionella in the sample.

10. A set of isolated nucleic acids, wherein a first nucleic acid is fully complementary or identical to a nucleotide sequence of probe 2695 (SEQ ID NO: 27), probe 2701 (SEQ ID NO: 25), or a nucleic acid of claim 1, and wherein a second nucleic acid is difference than said first nucleic acid, and is fully complementary or identical to a nucleotide sequence of one of probes 2704 (SEQ ID NO: 1), 2705 (SEQ ID NO: 2), 2708 (SEQ ID NO: 3), 2690 (SEQ ID NO: 4), 2957 (SEQ ID NO: 5), 2929 (SEQ ID NO: 6), 2954 (SEQ ID NO: 7), 2697 (SEQ ID NO: 15), or 2696 (SEQ ID NO: 26).

11. A set of claim 10, wherein said first nucleic acid is fully complementary or identical to a nucleotide sequence of probe 2704, 2695, 2705, or 2701, and said second nucleic acid is fully complementary or identical to a nucleotide sequence of probe 2697, 2696, or 2690.

12. A set of claim 11, wherein said nucleic acid set consists of probes 2704 and 2697, 2695 and 2696, or 2705 and 2690.

13. A set of isolated nucleic acids which hybridizes preferentially to 23S or 16S rRNA or rDNA of *Legionella micdadei* bacteria and not to non-*Legionella micdadei* organisms, wherein a first nucleic acid of said set is a nucleic acid of claim 4, and wherein said set comprises probes 2958 and 2968, probes 2956 and 2958, or probes 2699 and 2695.

14. An isolated nucleic acid of claim 1 which hybridizes preferentially to 23S rRNA or rDNA of *Legionella pheumophila* bacteria and not to non-*Legionella pneumophila* organisms, wherein said nucleic acid is fully complementary or identical to a nucleotide sequence of one of probes 2957 (SEQ ID NO: 5), 2929 (SEQ ID NO: 6), and 2954 (SEQ ID NO: 7).

15. A probe comprising a nucleic acid of claim 14 and a detection or enhancement moiety.

16. A method of detecting the presence of *Legionella pneumophila* in a sample suspected of containing Legionella bacteria comprising a) contacting the sample with at least one isolated nucleic acid of claim 14, b) imposing hybridization conditions on the sample and said isolated nucleic acid to allow the formation of a hybridization product between said nucleic acid and rRNA or rDNA from *L. pneumophila* bacteria, if present in the sample, but not from rRNA or rDNA from non-*L. pneumophila* bacteria; and c) detecting the hybridization product as an indication of the presence of *L. pneumophila* in the sample.

17. An isolated nucleic acid of claim 4 which hybridizes preferentially to 16S rRNA or rDNA of *Legionella micdadei* bacteria and not to non-*Legionella micdadei* organisms, wherein said nucleic acid is fully complementary or identical to a nucleotide sequence of probe 2699 (SEQ ID NO: 8).

18. A probe comprising a nucleic acid of claim 17 and a detection or enhancement moiety.

19. A method of detecting the presence of *Legionella micdadei* in a sample suspected of containing Legionella bacteria comprising a) contacting the sample with at least one isolated nucleic acid of claim 17, b) imposing hybridization conditions on the sample and said isolated nucleic acid to allow the formation of a hybridization product between said nucleic acid and rRNA or rDNA from *L. micdadei* bacteria, if present in the sample, but not from rRNA or rDNA from non-*L. micdadei* bacteria; and c) detecting the hybridization product as an indication of the presence of *L. micdadei* in the sample.

* * * * *

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:1:

TCGCCATCTG TCTAGCAAGC TAGACAATGC T        31

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:2:

ACTTTTAAGG ATTTGCTCCA GGTCGCCCCT        30

( 2 ) INFORMATION FOR SEQ ID NO:3:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:3:

ACTACGACCG ACTTTTAAGG ATTTGCTCCA G        31

( 2 ) INFORMATION FOR SEQ ID NO:4:

( i ) SEQUENCE CHARACTERISTICS:
        ( A ) LENGTH: 36 base pairs
        ( B ) TYPE: nucleic acid ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:4:

TAGAGTCCCC ACCATCACAT GCTGGCAACT AAGGAT         36

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:5:

TCAATGACTT CTCTATACCA AAAGGGTCAG AACCAC         36

( 2 ) INFORMATION FOR SEQ ID NO:6:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:6:

CTCTATCGCC AACTTTCCCA AATTGTTCTA C              31

( 2 ) INFORMATION FOR SEQ ID NO:7:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:7:

GCACCTCAGA GTTATGGAAA ACCGGATTTG C              31

( 2 ) INFORMATION FOR SEQ ID NO:8:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:8:

TTCGTCACTA ACCTCATTCA TAAGGCCAAC AACT           34

( 2 ) INFORMATION FOR SEQ ID NO:9:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:9:

CTGTATCGTG GTACTTCCCA GAACCTTCTA C        31

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:10:

GCCCACCTCT CAGTGAACCT TCTTCAGCCT        30

( 2 ) INFORMATION FOR SEQ ID NO:11:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:11:

GCACCTCAGC CTTAACAAGG GGCCGGATTT GC        32

( 2 ) INFORMATION FOR SEQ ID NO:12:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:12:

CCTCTTCAGC TCATTAAGCA TGTCAATTCA CC        32

( 2 ) INFORMATION FOR SEQ ID NO:13:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:13:

TCAATGACTT CTCCGCACAC CGTAGTGTCA GAACCAC 37

( 2 ) INFORMATION FOR SEQ ID NO:14:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:14:

TCGCCACCCA TCTAGTAAAC TAGACCGTGC T 31

( 2 ) INFORMATION FOR SEQ ID NO:15:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:15:

TTTCCCCAAG TTGTCCCCCT CTTCAAGGCA TAT 33

( 2 ) INFORMATION FOR SEQ ID NO:16:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:16:

TCTTAACCTA TCAACCCTCC TCCCCACTAG AAG 33

( 2 ) INFORMATION FOR SEQ ID NO:17:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:17:

AGGCGGTCAA CTTATCGCGT TTGCTGCGCC 30

( 2 ) INFORMATION FOR SEQ ID NO:18:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:18:

TAAGACCAAC TTTCGTTCCT GCTCGAGCCG T                                    31

( 2 ) INFORMATION FOR SEQ ID NO:19:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:19:

TCAGACTCGA TTTCTCTACG GCTCCCTTAT                                      30

( 2 ) INFORMATION FOR SEQ ID NO:20:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:20:

GCACACTTCT CAATGCACCT TCATCAGCCT                                      30

( 2 ) INFORMATION FOR SEQ ID NO:21:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:21:

CACAGTCATC ATCAAAGTCC AGTGCAAAAC T                                    31

( 2 ) INFORMATION FOR SEQ ID NO:22:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:22:

CCTCTCCAGC TCTGAAAGTA AATCCCATCA CC                                   32

( 2 ) INFORMATION FOR SEQ ID NO:23:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i i ) HYPOTHETICAL: NO ( i v ) ANTI-SENSE: NO ( x i ) SEQUENCE DESCRIPTION: SEQ ID NO:23:

TGTCCGACCG TACCGAGGGT ACCTTTGTGC T        31

( 2 ) INFORMATION FOR SEQ ID NO:24:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i i ) HYPOTHETICAL: NO ( i v ) ANTI-SENSE: NO ( x i ) SEQUENCE DESCRIPTION: SEQ ID NO:24:

CGGTACGGTT CTCTGTAAGT TATGGCTAGC GGC        33

( 2 ) INFORMATION FOR SEQ ID NO:25:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i i ) HYPOTHETICAL: NO ( i v ) ANTI-SENSE: NO ( x i ) SEQUENCE DESCRIPTION: SEQ ID NO:25:

TCGGACGCAG GCTAATCTTA AAGCGCCAGG CC        32

( 2 ) INFORMATION FOR SEQ ID NO:26:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i i ) HYPOTHETICAL: NO ( i v ) ANTI-SENSE: NO ( x i ) SEQUENCE DESCRIPTION: SEQ ID NO:26:

TTCATATGGC CAACAGCTAG TTGACATCGT TTAC        34

( 2 ) INFORMATION FOR SEQ ID NO:27:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i i ) HYPOTHETICAL: NO ( i v ) ANTI-SENSE: NO (xi) SEQUENCE DESCRIPTION: SEQ ID NO:27:

```
TGTCAGTATT AGGCCAGGTA GCCGCCTTCG                                30
```